United States Patent
Brooks

(10) Patent No.: US 6,855,134 B2
(45) Date of Patent: Feb. 15, 2005

(54) DISPOSABLE ABSORBENT ARTICLES WITH SKIN HEALTH AND ODOR CONTROL ADDITIVES

(75) Inventor: JoAnn Brooks, Arlington, TX (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 103 days.

(21) Appl. No.: 10/215,961

(22) Filed: Aug. 8, 2002

(65) Prior Publication Data

US 2004/0030315 A1 Feb. 12, 2004

(51) Int. Cl.[7] .................. A61F 13/00; A61F 13/15
(52) U.S. Cl. ................ 604/304; 604/359; 604/360
(58) Field of Search .................. 604/359, 360, 604/289, 304, 385.06; 602/48

(56) References Cited

U.S. PATENT DOCUMENTS

| | | | | |
|---|---|---|---|---|
| 4,838,253 A | | 6/1989 | Brassington et al. | |
| 5,635,191 A | * | 6/1997 | Roe et al. | 424/402 |
| 5,938,649 A | * | 8/1999 | Ducker et al. | 604/363 |
| 5,952,088 A | | 9/1999 | Tsai et al. | |
| 6,118,041 A | * | 9/2000 | Roe et al. | 604/360 |
| 6,197,237 B1 | | 3/2001 | Tsai et al. | |
| 6,203,810 B1 | * | 3/2001 | Alemany et al. | 424/404 |
| 6,485,733 B1 | * | 11/2002 | Huard et al. | 424/402 |
| 6,498,284 B1 | * | 12/2002 | Roe | 604/381 |
| 6,733,773 B1 | * | 5/2004 | Hsu et al. | 424/443 |
| 2002/0128615 A1 | * | 9/2002 | Tyrrell et al. | 604/364 |
| 2003/0119395 A1 | * | 6/2003 | Brooks | 442/96 |
| 2004/0030283 A1 | * | 2/2004 | Brooks | 604/48 |

* cited by examiner

*Primary Examiner*—Larry I. Schwartz
*Assistant Examiner*—Michael G Bogart
(74) *Attorney, Agent, or Firm*—Brinks Hofer Gilson & Lione

(57) ABSTRACT

The present invention relates to disposable absorbent articles comprising skin health and odor control additives for the treatment and prevention of skin irritation. The skin health treatment additive comprises an oil soluble wax that forms a tight lattice to protect the skin, and vitamins, lipids and triglycerides to protect and replenish the skin. Such disposable absorbent articles of the present invention are especially advantageous for the treatment and skin breakdown leading to partial full thickness wounds or pressure ulcers.

14 Claims, 1 Drawing Sheet

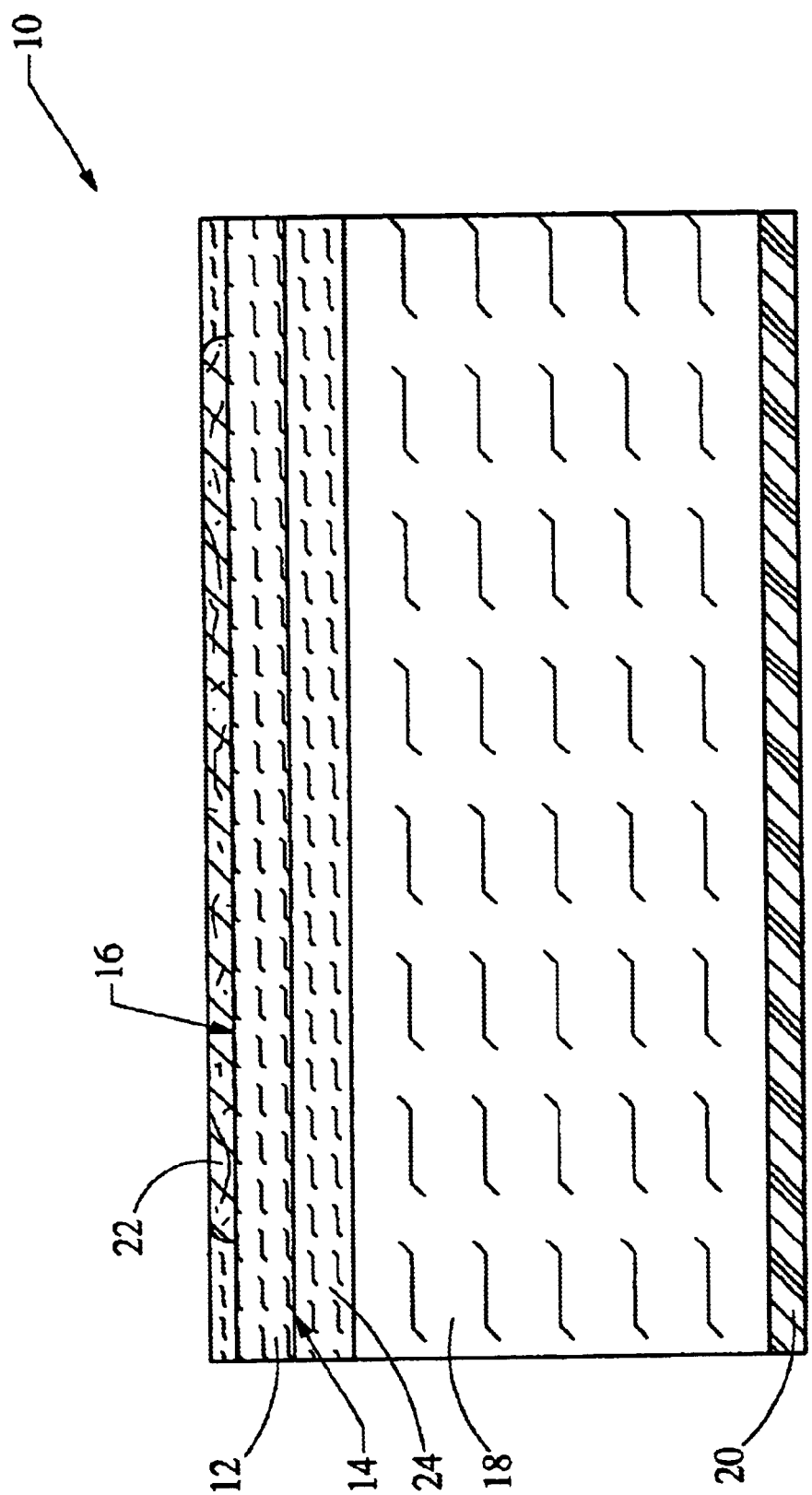

DISPOSABLE ABSORBENT ARTICLES WITH SKIN HEALTH AND ODOR CONTROL ADDITIVES

FIELD OF THE INVENTION

The invention relates to disposable absorbent articles containing skin health treatment additives and odor control additives. These disposable absorbent articles contain discreet localized deposits of a skin health treatment additive applied to the various layers of the article that will come into contact with the skin of a wearer. In particular, these disposable absorbent articles are useful as garments for incontinent adults for protecting the skin from irritating body fluids and fecal enzymes that may cause contact dermatitis and subsequent skin breakdown.

BACKGROUND OF THE INVENTION

The skin is a natural barrier to the penetration of foreign substances. The stratum corneum is the superficial cornified layer of the skin which provides a barrier to water evaporation and reduces the permeation of undesirable molecules from the external environment. The stratum corneum consists of dead cells called corneocytes, that are embedded in a lipid-rich matrix of fatty-acids, ceramides, and cholesterols. This structure of corneocytes embedded in lipids is thought to provide many of the barrier properties of the skin. Substances deposited on the skin must traverse this structure through a tortuous path to gain access to the underlying viable layers of the skin. Skin inflammation occurs when substances that are irritating to the skin are able to penetrate this barrier and initiate an elaborate cascade of immunological events once they contact the skin cells in the viable epidermis and dermis layers. As the skin barrier is compromised, the skin is subject to inflammatory events from percutaneous absorption of irritants through the stratum corneum.

Skin barrier function can be compromised by a variety of insults that cause inflammation. Insults to the skin can include, but are not limited to, environmental irritants, mechanical abrasion, continuous tissue load pressure, exposure to body fluids and waste, and exposure to chemicals. For example, physical and chemical treatments, abrasion, tape stripping, ultrasonics, electrical fields, enzymes, solvents, surfactants, and elevated ambient humidity are known to diminish skin barrier function. Bodily fluids and wastes may contain skin irritants in the form of enzymes such as proteases, ureases and lipases. Enzymes found in feces cleave the epidermis, dermis, and stratum corneum proteins and lipids and cause the breakdown of the natural barrier of the skin. Bacterial ureases on the skin convert the urea from urine to ammonia on the skin, causing an alkaline pH and leading to irritation of the skin. Prolonged exposure of the skin to these enzymes is thought to be a major cause of skin damage that leads to subsequent skin breakdown and contact dermatitis. In addition, the care of skin in individuals with ostomies is difficult due to the frequent contact of digestive enzymes with the skin surrounding the ostomy site. These enzymes can degrade the skin surface and cause severe skin breakdown and the development of partial thickness wounds.

Of particular concern is the formation of pressure ulcers in incapacitated individuals, such as bed-ridden patients, mentally challenged persons who are unable to perform personal hygiene, individuals who are incontinent, or hospital patients recovering from surgery to accidental trauma. These individuals may be subject to the formation of pressure ulcers due to prolonged tissue loads on parts of the body resulting from long periods of remaining in a stationary position, exposure of the skin to feces and urine, or a combination of these circumstances. Pressure ulcers frequently occur in the sacral coccyx area of the spine, however, these ulcers can also occur on hips, feet, and the skin covering elbows and shoulder blades.

A number of approaches are known for protecting the skin against the action of skin irritants and subsequent skin breakdown. Examples include protective apparel, skin protectant formulations, and anti-inflammatory compositions. Protective apparel garments may prevent irritants from contacting the skin, or may be used to prevent dissemination of irritants from bodily fluids to the surrounding environment, for example, diapers or adult incontinence garments. However, the use of barrier materials in these garments prevents movement of moisture and air and therefore, proliferates an environment in which skin may be kept in contact with the irritants and increase the damage.

Many of the skin protectant formulations commercially available may not provide adequate protection against skin irritants. Many of these formulations consist of petrolatum which can rub off onto garments and may affect the absorbency of disposable absorbent articles used as protective apparel.

Disposable absorbent products currently find widespread use in many applications. For example, in the infant and child care areas, diapers and training pants have generally replaced reusable cloth absorbent articles. Other typical disposable absorbent products include feminine care products such as sanitary napkins or tampons, adult incontinence products, and health care products such as surgical drapes or wound dressings. A typical disposable absorbent product generally comprises a composite structure including a top sheet, a back sheet, and an absorbent structure between the top sheet and back sheet. These products usually include some type of fastening system for fitting the product onto the wearer.

Disposable absorbent products are typically subjected to one or more liquid insults, such as exposure to urine, menses, blood, and feces during use. As such, the outer cover back sheet materials of the disposable absorbent products are typically made of liquid-insoluble and liquid impermeable materials, such as polypropylene films, that exhibit a sufficient strength and handling capability so that the disposable absorbent product retains its integrity during use by a wearer and does not allow leakage of the liquid insulating the product. These products are used for incontinent adults, especially bed-ridden or incapacitated individuals. The combination of skin contact with urine and feces, and the lack of air flow in garments consisting of these disposable absorbent articles can contribute to the irritation of skin leading to the development of partial and full thickness wounds and pressure ulcers.

An additional area of concern to care recipients and care givers alike is the effective management of odors arising from urinary incontinence. Soiled clothes, bedding, and disposable incontinence garments and pads can generate malodorous compounds such as isovaleric acid and other short chain organic acids, trimethylamine, ammonia, and a wide range of sulfides including dimethyl disulfide and dimethyl sulfide. The natural flora on the skin surface contain bacterial ureases which are responsible for the biotransformation of urea from urine into ammonia which is the most noticeable malodor in acute care, long term care and a home based caregiver settings. The organisms most frequently associated with the development of the above cited malodorous compounds are *Klebsiella pneumoniae, Eschericia coli,* and *Proteus mirabilis.* Other species present as normal flora can include a vast variety of gram negative and positive bacteria and fungi. The dominant offensive malodors arising from urine biotransformation and urine decomposition are sulfurous compounds and ammonia.

Past approaches to the problem have resulted in partial control of some of the odors present, notably ammonia. These approaches have included chelating chemistries such as disodium EDTA, adsorption materials such as activated carbon or charcoal and zeolites, and partially neutralized acrylic acid polymers. Combinations of these additives are well known in the art.

The development of malodorous compounds has been shown to be delayed for several hours during the effective wear period of the garment (5–8 hours) by the application of a wide range of anti-microbial compounds including mild cosmetic preservatives such as methylparaben, ethylparaben, or butylparaben.

Of particular use are sparingly water soluble and water insoluble compounds which are thought to impact the normal flora of the skin in a minimal way since they are not carried by the moisture of urine on the pad to the skin surface. Maintaining the normal flora is an important consideration in the management of healthy skin. Concerns about the development of resistant strains of bacteria has brought about the need for effective management of incontinence odors without aggressing the normal flora of the care recipient.

What is needed in the art are disposable absorbent articles comprising skin health treatment additives that can be pre-applied to the absorbent article to provide the skin with a barrier to prevent contact with irritants. What is also needed in the art are disposable absorbent articles comprising odor control additives. These and other needs are provided by the present invention.

SUMMARY OF THE INVENTION

The invention relates to disposable articles comprising skin health treatment additives. More particularly, the invention relates to disposable absorbent adult incontinence articles comprising discreet localized deposits of a skin health treatment additive applied to the layer of the article that will come into contact with the skin of a wearer and odor control additives. The disposable absorbent articles comprise a liquid permeable top sheet, an absorbent structure, a liquid impermeable back sheet, and a skin health treatment additive, wherein the skin health treatment additive is applied consistently and uniformly to the top sheet in a discreet area of a regional zone corresponding to the sacral-coccyx area of the spine.

FIG. 1 is a schematic depiction of the layers of the absorbent article of the present invention.

DETAILED DESCRIPTION OF THE INVENTION

A disposable absorbent article 10 of the present invention comprises a top sheet 12 having an inner surface 14 oriented toward an interior of the absorbent article and an outer surface 16 oriented toward an epidermal surface of a wearer of the article 10, an absorbent structure 18, a liquid impermeable back sheet 20, and a skin health treatment additive 22 applied to the surface of the article that will come into contact with the skin of the wearer 16. The absorbent structure 18 can be positioned between the top sheet and the back sheet 20. Alternatively, a fluid acquisition layer 24 can be added to the disposable absorbent article 10. The skin health additive 22 can be applied consistently and uniformly to the surface of the top sheet 12 in an area that will come into contact with the sacral and coccyx area of the wearer.

Non-migrating antimicrobials including, but not limited to, polychlorinated hydantoins such as n-halamine from HaloSource and silicone quaternary amines, from Aegis Environmental in Medland, Mich., are especially suited for odor control management in urinary incontinence of the frail elderly who are at risk for the development of antibiotic resistant strains of bacteria.

For the present invention, suitable odor control additives can include a chelating agent such as disodium EDTA in the range of 2%, an insoluble chlorinated hydantoin styrene bead in the range of 1.5–2.5%, a partially neutralized acrylic acid absorbent material coated with a silicone quaternary amine and present in 8–10%, a sparingly soluble antimicrobial such as methylparaben in the range of 0.5–1.0%, an anti-bioadhesion material such as zosteric acid present in 2–3%, a pH controlling organic acid such as malic acid present at 0.3–0.8%, a fluffed cellulose which has been pretreated with water soluble antimicrobials such as diazolidinyl urea at 0.5–0.8%, or combinations thereof.

The skin health treatment additive comprises at least one skin replenishing compound. Advantageously, the skin health treatment additive can comprise anti-inflammatory compounds, topical antibiotics, vitamins, enzyme blocking compounds, or combinations thereof.

Skin replenishing compounds include, but are not limited to emollients. Emollients are natural or synthetic compounds that soften, sooth, coat, lubricate or moisturize the skin. Emollients include, but are not limited to, fats, waxes, polar lipids, triglycerides, and esters. Emollients can be siloxane, silicone, or polysolixane based, or combinations thereof. Emollients suitable for the present invention include Huls Softisan 378 triglyceride wax, obtained from Condea Chemie/Condea Vista of Houston, Tex.

The skin health treatment additives of the present invention can comprise vitamins to help treat skin that has been irritated. Vitamins that are suitable for the present invention include, but are not limited to, vitamins A, C, and E. Preferably the skin health treatment additive of the present invention can comprise oil soluble vitamin C, vitamin A, and vitamin E. Barnett BVOSC is a vitamin C commercially available from Barnet Products, Retinyl Palmitate is a suitable vitamin A and Tocopherol Acetate is a suitable vitamin E, both commercially available from Roche, Nutlye, N.J. Vitamins can be present in amounts ranging from about 0.1% to about 0.5% of the composition.

Enzyme blocking compounds prevent skin irritation by blocking the ureases, and proteases or enzymes in feces and urine that can cause the breakdown of the natural protective barrier of the skin. Enzyme blocking compounds suitable for the present invention include any compound having inhibitory activity against proteolytic and/or lipolytic enzymes including, but not limited to, lipase, carboxypeptidase A, chymotrypsin, urease, elastase, trypsin, and leucine aminopeptidase. Enzyme blocking compounds suitable for the present invention can include, but are not limited to, any zinc compound. Suitable zinc compounds include, but are not limited to, zinc oxide, zinc sulfate or zinc lactate. Disodium EDTA is also a suitable enzyme blocking compound.

For administration to the skin of a human, the compositions will often be formulated to contain one or more preservatives. Preservatives that are suitable for the present invention include, but are not limited to isopropylparaben, isobutylparaben, and butylparaben. Advantageously, disodium EDTA is a preservative adjuvant which is a chelating agent that can bind and inactivate ureases, lipases and other enzymes.

Disposable absorbent articles suitable for the present invention can comprise a composite structure including a top sheet, a back sheet, and an absorbent structure between the top sheet and the back sheet. Accordingly, the article can further comprise a fluid acquisition layer. The liquid impermeable back sheet comprises a liquid repellant or water-barrier polymer material. The water-barrier material commonly used includes polymer materials, such as polyethylene film or copolymers of ethylene and other polar and non-polar monomers. The purpose of the water-barrier layer is to minimize or prevent absorbed liquid that may, during use, exude from the absorbent component and soil the user or adjacent clothing or environment. The water-barrier layer also has the advantage of allowing greater utilization of the absorbent capacity of the product and must exhibit a sufficient strength and handling capacity so that the disposable absorbent product retains its integrity during use by the wearer.

The absorbent structure between the top sheet and back sheet can be any biocompatible absorbent material comprising natural or synthetic components. The structure can comprise fibers, woven or non-woven materials, a web, a sponge, a matrix, fluffed cellulose superabsorbent material, or any combination thereof.

The top sheet comprises any biocompatible natural or synthetic material that will feel soft against the skin of the wearer, allow moisture and air to transpire, and not cause allergic or toxic reactions by the skin. Disposable absorbent articles suitable for the present invention include those disclosed in U.S. Pat. Nos. 6,306,782, 6,197,237, and 5.952,088 assigned to Kimberly Clark Worldwide, which are incorporated herein by reference.

The absorbent structure can comprise partially neutralized acrylic acid polymers in a fluffed cellulose matrix comprising enzyme blocking and odor control chemicals such as disodium EDTA, zinc lactate, zinc chloride, zinc oxide, and zinc sulfate evenly disposed in the absorbent layer matrix. Preferably, the odor control chemicals comprise 1.5–2.5% of the total weight of the product. In addition, the absorbent matrix can comprise an antimicrobial to minimize the development of odors arising from the biotransformation of lipids, apocrine sweat, and proteins by bacteria on the skin or from body fluids. Examples of suitable antimicrobials include but are not limited to, methylparaben, ethylparaben, butylparaben, diazolidinyl urea, imidazolidinyl urea, miconazole nitrate, 2-Bromo-2-Nitropropane-1, 3-Diol, dichlorobenzyl alcohol, DMDM Hydantoin and Iodopropynyl Butylcarbamate crystals, or non-leaching antimicrobials such as a n-halamine, or silicone quaternary amines. These antimicrobials can be used alone or in compatible mixtures. The amount of these will range from 0.25–2.5% of the total weight of the product.

The absorbent matrix can comprise a pH regulating organic acid such as malic, citric, tartaric, mandellic, lactic, maleic or glycolic acid. The addition of these acids should be in sufficient quantity to maintain an optimum skin pH of 4.2–4.8. The amount added should be titrated so as not to interfere with the absorbency of the partially neutralized acrylic acid super absorbent particles contained in the absorbent layer. The amount may range from 0.3–0.6% of the total weight of the product. The lowered pH is regarded to minimize the effect of skin damaging enzymes in feces and the bacterial urease biotransformation of urea in urine to ammonia.

The backsheet of the layer furthermost from the body can be a bilayer component composed of an extruded polyurethane foam with a breathable polyethylene outer layer. This layer will serve to cushion the sacral-coccyx area of the spine and allow air circulation to minimize the buildup of humidity as the garment is worn. Advantageously, this layer can be inserted into an area of the article which will correspond to the region of the sacral-coccyx area of the spine commonly known as the tailbone. The preferred shape of this insert is a rectangle of 5×7 inches.

Typically the packaging in which the disposable article is distributed is made from a water-barrier, specifically water-resistant, material. Water-resistivity is necessary to prevent the degradation of the packaging from environmental conditions and to protect the disposable articles therein.

This invention is further illustrated by the following examples, which are not to be construed in any way as imposing limitations upon the scope thereof. To the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

A formula for a skin health additive for a disposable absorbent article is prepared by combining the following ingredients by any method known in the art:

| Trade/common Name | INCI/CTFA | Proposed Amount | Vendor/ Location |
|---|---|---|---|
| Lipid/Vitamin/ Silicone skin health treatment additive | | | |
| Softisan 378 | Caprylic Capric/Stearic Triglyceride | QS to 100% (carrier or vehicle) | Condea/Chemie Houston, TX |
| Vitamin E | Tocopberol | 0.2–5% | Roche, Nutley, NJ |
| Dow Corning 580 Wax | Stearoxytri-methylsilane (and) Stearyl alcohol | 2–10% | Dow Corning, Midland, MI |
| Shea Butter Enzyme blocking compounds | Shea Butter | 1–5% | Henkel, NJ |
| Versene Na Antimicrobials | Disodium EDTA | 1.5–2.5% | Dow Chemical, Midland, MI |
| Methylparaben | Methylparaben | 0.5–1.0% | Nipa, Wilmington, DE |
| Poly 1 Cl PH adjusting organic acid | n-halamine | 1.8–2.5% | HaloSource |
| Maleic Acid Preservative (for the lipid/vitamin/silicone complex) | Maleic Acid | 0.2–0.5% | Alfa Chem, Kings Point, NY |
| Isopropylparaben, and isobutylparaben and butylparaben | LiquaPar Oil | 0.1–0.3% | Sutton Laboratories, Chatham, NJ |

The resulting anhydrous formula is heated to obtain a fluid homogeneous state (from about 70° C. to about 90° C.) and applied to the absorbent article. The coating can be applied by suitable methods apparent in the art including, but not limited to, spray application, slot coating, bead coating, rotary silk screening processes, evaporative coating, extrusion, or any combination thereof. The skin health treatment additive can be applied in a geometric pattern or a random pattern. A uniform and consistent coating with the skin health treatment additive is thought to provide maximum protection to the skin. Advantageously, the coated area can be in the geometric form of a circle, oval, square, rectangle, triangle, or combination, that is positioned on the top sheet of the article in a discreet location that would contact the skin of the sacral/coccyxx anatomical region, or tailbone, of the wearer. Preferably, the coated area is in the form of an elongated oval. The skin health additive can be applied in a criss-cross continuous pattern that allows indentations of fluid intake holes in the fluid acquisition skin contact layer. The skin health additive can be applied to the innermost skin contact layer.

Although particular aspects of the invention have been described, it would be obvious to one skilled in the art that various other modifications can be made without departing from the spirit and scope of the invention. It is therefore intended that all such changes and modifications are within the scope of the appended claims.

What is claimed is:

1. A disposable absorbent article comprising:
   a top sheet having an inner surface oriented toward an interior of the absorbent article and an outer surface, oriented toward an epidermal surface of a wearer of the article;
   an absorbent structure;
   a liquid impermeable back sheet;
   an anhydrous skin health treatment additive comprising:
      stearoxytrimethylsilane and stearyl alcohol present in an amount between 2 and 10 percent;
      disodium EDTA present in an amount between 1.5 and 2.5 percent;
      methyl-paraben present in an amount between 0.5 and 1.0 percent, and;
      n-halamine present in an amount between 1.8 and 2.5 percent;
   wherein the absorbent structure is positioned between the top sheet and the back sheet; and wherein the skin health treatment additive is applied consistently and uniformly to the top sheet in a discreet area of contact to the sacral and coccyx area of the wearer.

2. The disposable article of claim 1, wherein the skin health treatment additive comprises a therapeutically effective amount of emollients and vitamins in a triglyceride wax carrier.

3. The disposable article of claim 1, wherein the skin health treatment additive is applied in a geometric pattern selected from a square, a rectangle, a circle, a triangle, an oval, or combinations thereof.

4. The disposable article of claim 1, wherein the skin health treatment additive is applied in a criss cross continuous pattern.

5. The disposable article of claim 1, wherein the article is selected from a diaper, an adult incontinence article, feminine pad or a wound dressing.

6. The disposable article of claim 3, wherein the geometric pattern is an elongated oval.

7. An adult incontinence absorbent article comprising a liquid permeable top sheet; a fluid acquisition layer; an absorbent structure; a liquid impermeable back sheet; and an anhydrous skin health treatment additive comprising stearoxytrimethylsilane and stearyl alcohol present in an amount between 2 and 10 percent; disodium EDTA present in an amount between 1.5 and 2.5 percent; methyl-paraben present in an amount between 0.5 and 1.0 percent, and; n-halamine present in an amount between 1.8 and 2.5 percent; wherein the skin health treatment additive is applied consistently and uniformly to a discreet area of the top sheet, wherein the discreet area contacts the skin of a sacral or coccyx area of a wearer of the disposable article.

8. The adult incontinence absorbent article of claim 7, wherein the skin health treatment additive is applied in a criss/cross continuous pattern.

9. The adult incontinence absorbent article of claim 7, wherein the skin health treatment additive is applied to the coated area in a geometric pattern selected from a square, a rectangle, a circle, a triangle, an oval or combinations thereof.

10. The adult incontinence absorbent article of claim 9, wherein the geometric pattern is a rectangle.

11. The adult incontinence absorbent article of claim 7, wherein the skin health treatment additive further comprises vitamins, antibiotics, or medicaments.

12. A method of making a disposable absorbent article for providing treatment and protection to the sacral coccyx area of a wearer comprising:
   (a) providing a top sheet having an outer surface, an absorbent structure, a back sheet, and a skin health treatment additive applied to the outer surface comprising stearoxytrimethylsilane and stearyl alcohol present in an amount between 2 and 10 percent; disodium EDTA present in an amount between 1.5 and 2.5 percent; methyl-paraben present in an amount between 0.5 and 1.0 percent, and; n-halamine present in an amount between 1.8 and 2.5 percent;
   (b) applying the skin health treatment additive to a discreet area of the outer surface of the top sheet, wherein the additive is applied in a geometric pattern;
   (c) assembling the absorbent structure between the top sheet and the back sheet.

13. The method of claim 12, wherein the geometric pattern is a rectangle.

14. The method of claim 12, wherein the discreet area is positioned for contact with the skin of the sacral of coccyx area of a wearer of the article.

* * * * *